United States Patent [19]

Carlesso et al.

[11] Patent Number: 5,576,312
[45] Date of Patent: Nov. 19, 1996

[54] 1-AZATRICYCLO[7.2.0.0³,⁸]UNDEC-2-ENE-2-CARBOXYLATES AS ANTIBACTERIAL COMPOUNDS

[75] Inventors: Roberto Carlesso, Verona, Italy; Stuart Holman, Greenford, Great Britain; Alcide Perboni; Tino Rossi, both of Verona, Italy

[73] Assignee: Glaxo SpA, Verona, Italy

[21] Appl. No.: 381,873

[22] PCT Filed: Aug. 25, 1993

[86] PCT No.: PCT/EP93/02274

§ 371 Date: Feb. 21, 1995

§ 102(e) Date: Feb. 21, 1995

[87] PCT Pub. No.: WO94/05666

PCT Pub. Date: Mar. 17, 1994

[30] Foreign Application Priority Data

Aug. 27, 1992 [GB] United Kingdom ............ 9218240

[51] Int. Cl.⁶ .................. C07D 487/08; A61K 31/40
[52] U.S. Cl. ............................ 514/210; 540/302
[58] Field of Search ..................... 540/302; 514/210

[56] References Cited

U.S. PATENT DOCUMENTS 4,962,101 12/1990 DiNinno et al. .............. 514/210
4,978,659 12/1990 DiNinno et al. .............. 514/210

FOREIGN PATENT DOCUMENTS 416953 3/1991 European Pat. Off. .
422596 4/1991 European Pat. Off. .
502464 9/1992 European Pat. Off. .
507313 10/1992 European Pat. Off. .

OTHER PUBLICATIONS

Greene, T. W. *Protective Groups in Organic Synthesis* (John Wiley, New York), pp. 152, 153, 169, and 170 (1981).

*Primary Examiner*—Mukund J. Shah
*Assistant Examiner*—King Lit Wong
*Attorney, Agent, or Firm*—Bacon & Thomas

[57] ABSTRACT

The present invention relates to compounds of formula (I)

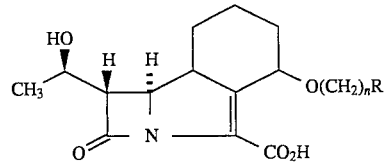

and salts and metabolically labile esters thereof; wherein R is a 5 or 6 membered nitrogen containing heteroaryl group, which heteroaryl group optionally contains 1 or 2 additional heteroatoms selected from nitrogen, oxygen or sulphur and said heteroaryl group is linked to the alkylene chain $(CH_2)n$ via a nitrogen atom in the heteroaryl group; n is an integer from 2 to 4, to processes for their preparation and to their use as antibacterial agents.

21 Claims, No Drawings

1-AZATRICYCLO[7.2.0.0³,⁸]UNDEC-2-ENE-2-CARBOXYLATES AS ANTIBACTERIAL COMPOUNDS

This invention relates to heterocylic compounds having antibacterial activity, to processes for their preparation, to compositions containing them and to their use in medicine.

In EPA No. 0416953A2 there is described 10-(1-hydroxyethyl)-11-oxo-1-azatricyclo[7.2.0.0.$^{3\cdot8}$]-undec-2-ene-2-carboxylic acid, and 4 substituted derivatives thereof, and salts and esters thereof, which compounds have antibacterial activity.

In EPA No. 0422596A2 there is described inter alia 10-(1-hydroxyethyl)-11-oxo-1-azatricyclo[7.2.0.0.$^{3\cdot8}$]-undec-2-ene-2-carboxylic and derivatives thereof and salts and metabolically labile esters thereof as having antibacterial activity.

We have now discovered a novel group of 4-substituted 10-(1-hydroxyethyl)-11-oxo-1-azatricyclo[7.2.0.0.$^{3\cdot8}$]-undec-2-ene-2-carboxylic acids and salts thereof which have useful antibacterial activity.

According to the present invention, therefore we provide compounds of general formula (I)

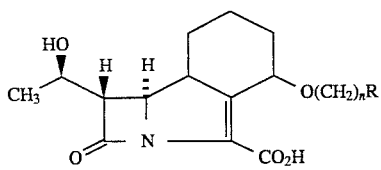

(I)

salts and metabolically labile esters thereof;
wherein R is a 5 or 6 membered nitrogen containing heteroaryl group which heteraryl group optionally contains 1 or 2 additional heteroatoms selected from nitrogen, oxygen or sulphur and said heteroaryl group is linked to the alkylene chain $(CH_2)_n$ via a nitrogen atom in the heteroaryl group;

n is an interger from 2 to 4.

In addition to the fixed stereochemical arrangement as defined in formula (I) the molecule contains a further asymmetric carbon atom at the 8-position, and another at the 4-position. It will be appreciated that all stereoisomers including mixtures thereof arising from these additional asymmetric centres, are within the scope of the compounds of formula (I).

Salts of compounds of formula (I) include base addition salts for use in medicine such salts are formed with bases that have a physiologically acceptable cation. Suitable cations include those of alkali metals (e.g. sodium or potassium), alkaline earth metals (e.g. calcium), amino acids (e.g. lysine and arginine) and organic bases (e.g. procaine, phenylbenzylamine, dibenzylethylenediamine, ethanolamine, diethanolamine, and N-methyl glucosamine).

Salts derived from bases wherein the cation is not physiologically acceptable may be useful as intermediates for the preparation and/or isolation of other compounds of the invention, and these salts also form part of the invention.

When the group R contains a basic centre, acid addition salts of such compounds and internal salts formed with the carboxylic acid grouping are also included in the invention.

It will be appreciated that the compound of formula (I) may be produced in vivo by metabolism of a suitable metabolically labile ester. Examples of suitable metabolically labile esters include acyloxyalkyl esters such as, acyloxymethyl or 1-acyloxyethyl e.g. pivaloyloxymethyl, 1-pivaloyloxyethyl, acetoxymethyl, 1-acetoxyethyl, 1-methoxy-1-methyl-ethylcarbonyloxyethyl, 1-benzoyloxyethyl, isopropoxycarbonyloxymethyl, 1-isopropoxycarbonyloxyethyl, cyclohexylcarbonyloxymethyl, 1-cyclohexylcarbonyloxyethyl ester, cyclohexyloxycarbonyloxymetyl, 1-cyclohexylcarbonyloxyethyl ester, cyclohexyloxycarbonyloxymethyl, 1-cyclohexyloxycarbonyloxyethyl, 1-(4-tetrahydropyranyloxycarbonyloxyethyl) or 1-(4-tetrahydropyranylcarbonyloxyethyl.

Examples of suitable heteroaryl groups R include triazole e.g. 1,2,3 triazole or 1,2,4 triazole, imidazole, pyrazole, pyridinium, pyrimidine, pyrazine, thiazole, thiazine, thiadiazole or triazine.

Where the heteroaryl ring contains a second nitrogen atom the invention also covers quaternary derivatives thereof such as $C_{1-4}$alkyl quaternary derivatives thereof.

The general formula (I) as drawn includes at least 4 stereoisomers and mixtures thereof and these may be represented by the formulae (1a, 1b, 1c and 1d).

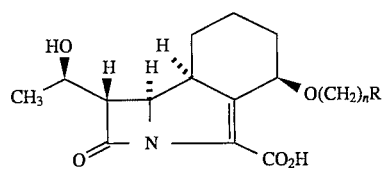

1a

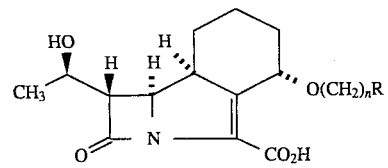

1b

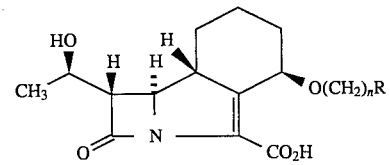

1c

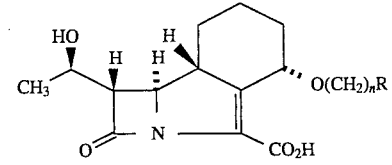

1d

The solid wedge shaped bond indicates that the bond is above the plane of the paper. The broken bond indicates that the bond is below the plane of the paper.

The configuration shown for the carbon atom at the 8-position in formulae 1a and 1b is hereinafter referred to as the β configuration and in formulae 1c and 1d as the α configuration.

The configuration shown for the carbon at the 4 position in formulae 1b and 1d is hereinafter referred to as the α configuration and in formulae 1a and 1c as the β configuration.

In general, in the specific compounds named below, the β-configuration at the 8-position corresponds to the S isomer and the β-configuration at the 4-position to the R isomer. The α configuration at the 8-position corresponds to the R isomer and the α-configuration at the 4-position corresponds to the S isomer. The assignment of the R or S configuration at the 4- and 8-positions have been made according to the rules of Cahn. Ingold and Prelog, Experientia 1956, 12, 81.

A preferred group of compounds of formula I are those in which the carbon atom at the 8-position is in the β configuration. Within this group those compounds in which the carbon atom at the 4-position is in the α configuration are particularly preferred.

A further preferred group of compounds of the invention are those in which n is 2 or 3 more particularly 2.

The group R is preferably a heteroaryl group containing from 1 to 3 nitrogen atoms. For example, pyridinum, imidazole, N-methylimidazolium, pyrazole, 1,2,3 triazole, or 1,2 4 triazole.

Specific preferred compounds include:

(4S,8S,9R,10S,12R)-10-(1-hydroxyethyl)-11-oxo-4-[2-(1,2,3-triazole-1-yl)ethoxy)]I-azatricyclo[7.2.0.0$^{3,8}$] undec-2-ene-2-carboxylic acid and salts thereof e.g. potassium or sodium salt.

(4S,8S,9R,10S,12R)-4-[2-(N-pyridinium)ethoxy]10-(1-hydroxyethyl)-II-oxo-I-azatricyclo[7.2.0.0$^{3-8}$]undec-2-ene-2-carboxylate.

Compounds according to the invention not only exhibit a broad spectrum of antibacterial activity against a wide range of pathogenic microorganisms but also have a very high resistance to all β-lactamases. Compounds of the invention are also relatively stable to renal dehydropeptidase.

Compounds of the invention have been found to exhibit useful levels of activity against strains of *Staphylococcus aureus, Streptococcus faecalis, Escherichia coli, Pseudomonas aeruginosa, Clostridium perfringens* and *Bacteriodes fragilis*.

The compounds of the invention may therefore be used for treating a variety of diseases caused by pathogenic bacteria in human beings and animals.

Thus, according to another aspect of the present invention, we provide a compound of formula (I) or a physiologically acceptable salt thereof for use in the therapy or prophylaxis of systemic or topical bacterial infections in a human or animal subject.

According to a further aspect of the invention we provide the use of a compound of formula (I) or a physiologically acceptable salt thereof for the manufacture of a therapeutic agent for the treatment of systemic or topical bacterial infections in a human or animal body.

According to a yet further aspect of the invention we provide a method of treatment of the human or non-human animal body to combat bacterial infections which method comprises administering to the body an effective amount of a compound of formula (I)m or a physiologically acceptable salt thereof.

The compounds of the invention may be formulated for administering in any convenient way for use in human or veterinary medicine and the invention therefore includes within its scope pharmaceutical compositions comprising a compound of the invention adapted for use in human or veterinary medicine. Such compositions may be presented for use in conventional manner with the aid of one or more suitable carriers or excipients. The compositions of the invention include those in a form especially formulated for parenteral, oral, buccal, rectal, topical, implant, ophthalmic, nasal or genito-urinary use.

The compounds according to the invention may be formulated for use in human or veterinary medicine by injection (e.g. by intravenous bolus injection or infusion or via intramuscular, subcutaneous or intrathecal routes) and may be presented in unit dose form, in ampoules, or other unit-dose containers, or in multi-dose containers, if necessary with an added preservative. The compositions for injection may be in the form of suspensions, solutions, or emulsions, in oily or aqueous vehicles, and may contain formulatory agents such as suspending, stabilising, solubilising and/or dispersing agents. Alternatively the active ingredient may be in sterile powder form for reconstitution with a suitable vehicle, e.g. sterile, pyrogen-free water, before use.

The compounds of the invention may also be presented for human or veterinary use in a form suitable for oral or buccal administration, for example in the form of solutions, gels, syrups, mouth washes or suspensions, or a dry powder for constitution with water or other suitable vehicle before use, optionally with flavouring and colouring agents. Solid compositions such as tablets, capsules, lozenges, pastilles, pills, boluses, powder, pastes, granules, bullets or premix preparations may also be used. Solid and liquid compositions for oral use may be prepared according to methods well known in the art. Such compositions may also contain one or more pharmaceutically acceptable carriers and excipients which may be in solid or liquid form.

The compounds of the invention may also be administered orally in veterinary medicine in the form of a liquid drench such as a solution, suspension or dispersion of the active ingredient together with a pharmaceutically acceptable carrier or excipient.

The compounds of the invention may also, for example, be formulated as suppositories e.g. containing conventional suppository bases for use in human or veterinary medicine or as pessaries e.g. containing conventional pessary bases.

The compounds according to the invention may be formulated for topical administration, for use inhuman and veterinary medicine, in the form of ointments, creams, gels, lotions, shampoos, powders, (including spray powders), pessaries, tampons, sprays, dips, aerosols, drops (e.g. eye ear or nose drops) or pour-ons.

Aerosol sprays are conveniently delivered from pressurised packs, with the use of a suitable propellant, eg dichlorodifluoromethane, trichlorofluoromethane, dichlorotetrafluoroethane, carbon dioxide or other suitable gas.

For topical administration by inhalation the compounds according to the invention may be delivered for use in human or veterinary medicine via a nebuliser.

The pharmaceutical compositions for topical administration may also contain other active ingredients such as corticosteroids or antifungals as appropriate.

The compositions may contain from 0.01–99% of the active material. For topical administration, for example, the composition will generally contain from 0.01–10%, more preferably 0.01–1% of the active material.

For systemic administration the daily dose as employed for adult human treatment will range from 5–100 mg/kg body weight, preferably 10–60 mg/kg body weight, which may be administered in 1 to 4 daily doses, for example, depending on the route of administration and the condition of the patient. When the composition comprises dosage units, each unit will preferably contain 200 mg to 1 g of active ingredient.

The duration of treatment will be dictated by the rate of response rather than by arbitrary numbers of days.

The compounds of formula (I) may be prepared from the compound of formula (II), wherein $R_1$ is a carboxyl protecting group and X is a leaving group such as halogen e.g. iodide and n is as defined in formula (I).

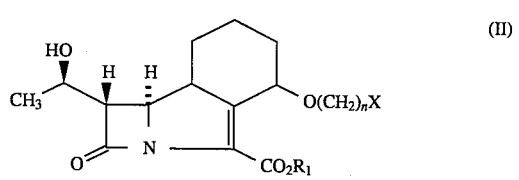

(II)

by reaction with the appropriate heteroarylamine or a protected derivative thereof, followed by removal of the protecting group $R_1$.

The reaction is preferably carried out in a polar aprotic solvent such as acetonitrile and preferably with heating e.g. 40°–80°.

If the desired reaction of the compound of formula (II) is with a secondary amino moiety in the heteroaryl group then it is preferable to convert the secondary amino group into the corresponding trimethylsilyl derivative prior to carrying out the reaction.

The compound of formula (I) wherein R is a 1,2,3 triazole grouping may be prepared by reaction of the azide (III) in which $R_1$ is a carboxyl protecting group and $R_2$ is a trialkylsilyl group.

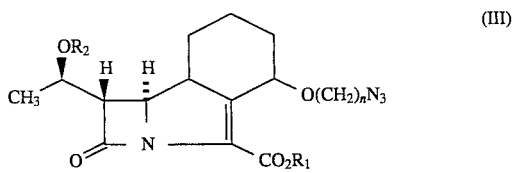

(III)

with trimethylsilylacetylene followed by reaction with tetra n-butylammonium fluoride and then subsequent removal of the carboxyl protecting group $R_1$.

The azides of formula (III) may be prepared from the corresponding alcohols of formula (IV)

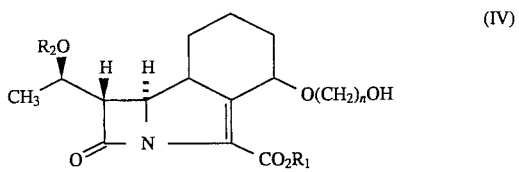

(IV)

by reaction with sodium azide in the presence of triphenylphosphine and carbontetrabromide. The reaction is preferably carried out in a polar aprotic solvent such as dimethylformamide.

The compounds of formula (II), (III), or (IV) may be prepared using the procedures described in WO92/15587.

The carboxyl protecting groups $R_1$ in formulae (ll), (lll) and (lV) is preferably a group that can be removed by hydrolysis under buffered conditions or under non-aqueous conditions.

Examples of such suitable carboxyl protecting groups $R_1$ include arylmethyl groups such as benzyl, p-nitrobenzyl or trityl, or alkenyl groups such as allyl or substituted allyl, t-butyl, haloalkyl e.g. trichloroethyl or trialkylsilylalkyl e.g. trimethylsilylethyl. Preferred protecting groups $R_1$ include arylmethyl e.g. benzyl or allyl.

The hydroxyl protecting groups $R_2$ in formulae (III) and (IV) is preferably a group which may be removed by hydrolysis under buffered conditions or under non-aqueous conditions.

Examples of particularly suitable protecting groups $R_2$ include those in which $R_2$ is a hydrocarbylsilyl group such as trialkylsilyl, e.g. trimethylsilyl or t-butyldimethylsilyl. $R_2$ may also represent an acyl group such as alkanoyl e.g. acetyl, pivaloyl; alkenoyl e.g. allylcarbonyl; aroyl e.g. p-nitrobenzoyl; alkoxycarbonyl e.g. t-butoxycarbonyl; haloalkoxycarbonyl e.g. 2,2,2-trichloroethoxycarbonyl, or 1,1,1-trichloro-2-methyl-2-propoxycarbonyl; aralkyloxycarbonyl e.g. benzyloxycarbonyl or P-nitrobenzyloxycarbonyl; or alkenyloxycarbonyl e.g. allyloxycarbonyl.

A particularly convenient protecting group $R_2$ is t-butyldimethylsilyl.

The hydroxyl and carboxyl protecting groups $R_2$ and $R_1$ may be removed by conventional procedures such as those described in Protective Groups in Organic Chemistry, pages 46–119, Edited by J F W McOmie (Plenum Press, 1973). For example when $R_2$ is a t-butyldimethylsilyl group, this may be removed by treatment with tetrabutylammonium fluoride and acetic acid. This process is conveniently carried out in a solvent such as tetrahydrofuran. Similarly when $R_2$ is a trichloroethoxycarbonyl group this may be removed by treatment with zinc and acetic acid.

The carboxyl protecting group $R_1$ may also be removed by standard processes such as those described in Protective Groups in Organic Chemistry, pages 192–210, Edited by J F W McOmie (Plenum Press 1973). For example when $R_1$ represents an arylmethyl group this may be removed by conventional procedures using hydrogen and a metal catalyst e.g. palladium. When the group $R_1$ represents an allyl or substituted ally group then this is preferably removed by treatment with an allyl acceptor in the presence of tetrakis(triphenylphosphine) palladium and optionally in the presence of triphenylphosphine. Suitable allyl acceptors include sterically hindered amines such as tertbutylamine, cyclic secondary amines such as morpholine or thiomorpholine, tertiary amines such as triethylamine, aliphatic or cycloaliphatic β-dicarbonyl compounds such as acetylacetone, ethyl acetoacetate or dimedone, tributyltin hydride or alkanoic acids or alkali metal salts thereof such as acetic acid, propionic acid or 2-ethyl hexanoic acid or the potassium or sodium salt thereof.

A particularly useful allyl acceptors included 2-ethylhexanoic acid and more especially the sodium or potassium salts thereof or tributyltin hydride.

The reaction is preferably carried out in an inert colvent such as an ether e.g. diethyl ether or tetrahydrofuran, an alkanol e.g. ethanol, an ester e.g. ethyl acetate or a halohydrocarbon e.g. methylene chloride, or mixtures thereof. The reaction is conveniently carried out in the temperature range 0°–40° more particularly at room temperature.

Base addition salts of compounds of formula (I) may be prepared from the parent acid by treatment with a suitable base. Conveniently the salt is formed in solution and then if required precipitated by the addition of a non-solvent e.g. a non polar aprotic solvent. Alternatively the sodium or potassium salt may be prepared by treating a solution of the parent acid of formula (I) with a solution of sodium or potassium 2-ethylhexanoate in a non-polar solvent such as diethyl ether.

In any of the formulae (I) to (IV) shown above when there is an asymmetric carbon atom and no specific configuration is shown then the formula includes all possible configurations.

Specific stereoisomers of the compounds of formula (I) as defined in formulae 1a, 1b, 1c and 1d, essentially free of the other stereoisomers may be prepared by using the general processes described above starting with the appropriate stereoisomers of formula (II).

In order that the invention may be more fully understood the following examples are given by way of illustration only.

In the Preparations and Examples, unless otherwise stated:

Melting points (m.p.) were determined on a Gallenkamp m.p. apparatus and are uncorrected. All temperatures refer to ° C.

Infrared spectra were measured in chloroform-$d_1$ solutions on a FT-IR instrument. Proton Magnetic Resonance (1H-NMR) spectra were recorded at 300 MHz as solutions in chloroform-$d_1$. Chemical shifts are reported in ppm downfield (δ) from $Me_4Si$, used as an internal standard, and are assigned as singlets (s), doublets (d), doublet of doublets (dd) or multiplets (m).

Column chromatography was carried out over silica gel (Merck AG Darmstadt, Germany).

Solutions were dried over anhydrous sodium sulphate.

"Petrol" refers to petroleum ether , b.p. 40°–60° C.

Methylene chloride was redistilled over calcium hydride; tetrahydrofuran was redistilled over sodium; ethyl ether was redistilled over sodium; xylene was redistilled over phosphorus pentoxide and ethyl acetate was dried over activated molecular sieves.

T.l.c. refers to thin layer chromatography on silica plates.

INTERMEDIATE 1

Allyl(4S,8S,9R,10S,12R)4-[2-(N-pyridinium)-ethoxy-]-10-(1-hydroxy -ethyl)-11-oxo-1-azatricyclo-[7.2.0.0$^{3.8}$]undec-2-ene-2-carboxylate iodide.

In a well stoppered flask, a solution of ally(4S,8S,9R, 10S,12R)-4-[2-(iodo)-ethoxy)-10-(1-hydroxyethyl)-11-oxo-1-azatricyclo-[7.2.0.0.$^{3.8}$]undec-2-ene-2-carboxylate (250 mg) and pyridine (214 mg) in dry acetonitrile (5 ml was stirred for 5 hr at 60° C. The solution was then evaporated under vacuum and the residue was triturated with a mixture of diethylether and petroleum to give the title compound (183 mg) which was used directly in the next step without purification.

IR (CDCl$_3$) max (cm$^{-1}$) 3410 (OH), 1774 (C=O), 1715 (C=O)

$^1$H-NMR δ(CDCl$_3$) 9.27 (d), 8.64 (t), 8.20 (m), 5.90 (m), 5.5–5.26 (m), 5.3–5.0 (m), 5.05 (t), 4.88–4.6 (m), 4.37 (dd), 4.21 (m), 4.0–3.8 (m), 3.18 (dd), 2.96 (m), 1.95 (m), 1.88 (m), 1.7–1.25 (m), 1.9 (d)

INTERMEDIATE 2

Allyl-(4S,8S,9R,10S,12R)-1-aza-4-t-butyldimethylsilyloxyethoxy-10-[1-(2-t-butyldimethylsilyloxy)ethyl]-11-oxo-1-tricylco [7.2.0.0$^{3.8}$]undec-2-ene-2-carboxylate (3S,4R)-3-[(R)-1-(t-butyldimethylsilyloxy)ethyl]4-[(R)-2'-[(S)-6'-(2-t-butylidimethylsilyloxyethoxy)-1'-oxocyclohexyl]]azetidin-2one (650 mg), (3S,4R)-3-[(R)-1-(t-butyldimethylsilyloxy)ethyl]-4-[(R)-2'-[(S)-6'-(2-t-butylidimethylsilyloxyethoxy)-1'-oxocyclohexyl]]azetidin-2-one (650 mg), potassium carbonate (250 mg) and methylene chloride (15 ml), were placed in a flask and stirred under a nitrogen atmosphere for 5 minutes. Triethylamine (0.3 ml) and allyl oxallylchloride (0.3 ml) were added and after three hrs a further 0.2 ml of both reactants were added. The mixture was stirred for further 2 hrs, quenched with water and extracted with methylene chloride. The organic layer was washed with hydrochloric acid (2.50 ml of 2% solution at 0° C.), sodium hydrogen carbonate (2×50 ml of 5% solution at 0° C.), dried over anhydrous sodium sulphate and concentrated under reduced pressure. The resultant oil which was dissolved in zylene (20 ml), hydroquinone (20 mg), triethylphosphite (1.2 ml) were added and the mixture was refluxed for 5 hrs. The reaction mixture was cooled at room temperature and concentrated under reduced pressure. The title compound was isolated by flash chromatography using cylcohexane/ethyl acetate as eluant (500 mg, RF-0.8).

IR, CDCl$_3$(cm$^{-1}$): 1769(C-O lactam), 1744(c=O).

INTERMEDIATE 3

Allyl (4S, 8S, 9R, 10S, 12R)-10-[1-(t-butyldimethylsilyloxy)-ethyl]-4-[2-hydroxyethoxy]-11-oxo-1-azatricyclo-[7.2.0.0.$^{3.8}$]undec-2-ene-2-carboxylate A solution of tetra-n-butylammonium fluoride in tetrahydrofuran (1.1M; 5.0 ml) was added to a solution containing intermediate 2 (2.8 g) and acetic acid (0.5 ml) in tetrahydrofuran (40 ml). The mixture was stirred at 20° under nitrogen for 18 hrs and was then diluted with ethyl acetate (120 ml). The solution was washed equentially with 5% aqueous hydrochloric acid (50 ml), saturated aqueous sodium bicarbonate (50 ) and saturated brine (50 ml), dried over anhydrous sodium sulphate and then evaporated under reduced pressure to an oil. The oil was purfied by chromatography on silica gel. Elution with cychohexane/ethyl acetate 1/1 gave the title compound as a pale yellow syrup (1.73 g) (Tlc, cyclohexane/ethyl acetate 1/1 Rf=0.6).

INTERMEDIATE 4

Allyl (4S,8S,9R,10S,12R)-4-[2-azidoethoxy]-10-[1-(t-butyldimethylsilyloxy)-ethyl]-11-oxo1-azatricyclo[7.2.0.0.$^{3.8}$]undec-2-ene-2-carboxylate A solution of carbontetrabromide (219 mg) in dry dimethylformamide (2 ml) was added dropwise over 20 mins to a stirred suspension containing intermediate 3 (228 mg), sodium azide (201 mg) and triphenylphosphine (184 mg in dry dimethylformamide (5 ml) at 20° under nitrogen. The mixture was thus stirred for 1 hr and was then diluted with diethyl ether (30 ml). The mixture was washed with saturated brine (3×20 ml), dried over anhydrous sodium sulphate and evaporated under reduced pressure to give an oil. This was purified by flash chromatography on silica gel. Elution with ethyl acetate/cyclohexane 1/4 gave the title compound (185 mg) as a colourless oil.

IR:$_{max}$ (CDCl$_3$) 2108, 1776, 1820 cm$^{-1}$

INTERMEDIATE 5

Allyl (4S,8S,9R,10S,12R)-10-[1-(t-butyldimethylsilyloxy)-ethyl]-4-[2-(4-trimethylsilyl-1.2.3-triazol-1-yl)ethoxy]-11-oxo-1-azatricyclo-[7.2.0.0.$^{3.8}$]undec-2-ene-2-carboxylate.

A solution of the intermediate 4 (1.18 g) in trimethylsilylacetylene (20 ml) was heated under reflux under nitrogen for 20 hrs. Solvent was then evaporated under reduced pressure and the residual oil was subjected to flash chromatography on silica gel. Elution using ethyl acetate/cyclohexane 1.4 gave the title compound as a colourless oil (0.63 g).

IR:$_{max}$ (CDCl$_3$) 1772, 1717, 1600 cm–$^1$;

$^1$H-NMR (300 MHZ, CDCl$_3$) 7.64(s), 5.95(m), 5.43(m), 5.26(m), 5.12(t), 4.82–4.6(m), 4.57(m), 4.21(m), 4.07(dd), 3.72(m), 3.16(dd), 2.80(m), 2.02(m), 1.8–1.2(m), 1. (d), 0.88(s), 0.33(s), 0.07(s).

INTERMEDIATE 6

Allyl (4S,8S, 9R, 10S, 12R)-10-[1-(hydroxyethyl]-11-oxo-4-[2-1,2,3-triazol-1-yl)ethoxy]-1-azatricyclo-[7.2.0.0.$^{3.8}$]undec-2-ene-2-carboxylate A solution of tetra-n-butylammonium fluoride in tetrahydrofuran (1.1M; 1.0 ml) was added to a solution of the intermediate 5 (100 mg) and glacial acetic acid (0.1 ml) in dry tetrahydrofuran (1.5 ml). The mixture was stirred under nitrogen at 22° for 23 hrs and then treated with a 5% solution of sodium hydrogen carbonate (30 ml). The mixture was extracted with ethyl acetate (2×50 ml) and the combined extracts were washed with brine (20 ml), dried over anhydrous sodium sulphate and evaporated under reduced pressure. The residual gum was purified by flash chromatography on silica gel. Elution with ethyl acetate gave the title compound as a colourless oil (47 mg).

IR:$_{max}$ (CDCl$_3$) 3611, 1776, 1720, 1620, 1603 cm$^{-1}$, $^1$H-NMR (300 MHZ, CDCl$_3$) 7.71(s), 7.66(s), 5.96(m), 5.43(m), 5.28(m), 4.8–4.6(m), 4.57(m), 4.21(m), 4.08(dd), 3.75(m), 3.19(dd), 2.75(m), 5.10(t), 2.32(m), 2.1–1.94(m), 1.92–1.60(m), 1.5–1.2(m), 1.31(d).

EXAMPLE 1

(4S,8S,9R,10S,12R)4-[2-(N-pyridinium)-ethoxy-]-10-(1-hydroxyethyl)-11-oxo-1-azatricyclo-[7.2.0.0$^{3,8}$]undec-2-ene-2-carboxylate To a solution of intermediate 1 (183 mg) in dry dichloromethane (5 ml), was added a solution of triphenylphosphine (18 mg), tetrakis (triphenylphosphine)palladium (19.6 mg) in dichloromethane (3 ml). Tributyltin hydride (138 mg) was then added and the obtained mixture was stirred for 60 min. The solid which precipitated was then triturateed several times with diethylether. The solid was then separated by centrifugation, then dried under vacuum to give the title compound (90 mg).

IR (nujol) max (cm$^{-1}$) 1757 (C=O), 1589 (C=C)

$^1$H-NMR δ(Acetone-D6, D$_2$O) 8.75 (m), 8.48 (m), 7.98 (m), 4.84 (m), 4.72–4.6 (m), 4.050 (m), 3.9–3.64 (m), 3.8 (dd), 3.61 (t), 3.22 (dd),2.42–2.3 (m), 1.88–1.74 (m), 1.68–1.54 (m), 1.54–1.3 (m), 1.2–1.1 (m), 1.08 (d)

EXAMPLE 2

(4S,8S,9R,10S,12R)-10-[1-(hydroxyethyl]-11-oxo-4-[2-1.2.3-triazol-1-yl)ethoxy]-1-azatricyclo-[7.2.0.0.$^{3,8}$]undec-2-ene-2-carboxylic acid, potassium salt A solution of potassium 2-ethylhexanoate in ethyl acetate (0.5M; 0.2 ml) was added to a solution of the intermediate 6 (40 mg), palladium tetrakis(triphenylphosphine) (2 mg) and triphenylphospine (2 mg) in dry tetrahydrofuran (0.5 ml). The mixture was stirred at 22° under nitrogen for 1 hr and then diluted with diethyl ether (5 ml). The resulting suspension was centrifuged and the supernatant decanted. The residual solid was triturated three times with diethyl ester (5 ml) and then dried in vacuo to give the title compound as a white powder (29 mg).

IR:$_{max}$ (CDCl$_3$) 1751, 1595 cm$^{-1}$;

$^1$H-NMR (300 MHZ, CDCl$_3$) 7.88(s), 7.70(s), 4.36(m), 4.7–4.4(m), 4.04(m), 3.9–3.8(m), 3.82–3.7(m), 3.79(dd), 3.60(m), 3.18(dd), 2.19(m), 1.76(m), 1.58(m), 1.5–1.3(m), 1.07(d).

We claim:
1. Compounds of formula (I)

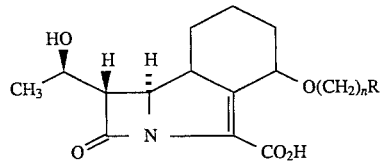

and salts and metabolically labile esters thereof; wherein R is a 5 or 6 membered nitrogen containing heteroaryl group, which heteroaryl group optionally contains 1 or 2 additional heteroatoms selected from nitrogen, oxygen or sulphur and said heteroaryl group is linked to the alkylene chain (CH$_2$)n via a nitrogen atom in the heteroaryl group; n is an integer from 2 to 4.

2. Compounds as claimed in claim 1 wherein R is a heteroaryl group containing from 1 to 3 nitrogen atoms.

3. Compounds as claimed in claim 1 wherein R is a pyridinium imidazole, N-methylimidazolium, pyrazole, 1,2,3 triazole or 1,2,4 triazole group.

4. Compounds as claimed in claim 1 wherein R is a 1,2,3 triazole or pyridinium group.

5. Compounds as claimed in claim 1 wherein n is 2 or 3.

6. Compounds as claimed in claim 1 wherein n is 2.

7. A compound as claimed in claim 1 having the configuration

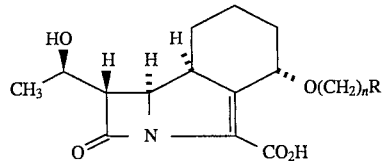

8. A method of treatment of a human or non-human body to combat bacterial infections comprising administration of an effective amount of a compound as claimed in claim 1.

9. Pharmaceutical compositions containing an effective amount of a compound as claimed in claim 1 admixture with one or more physiologically acceptable carriers or excipients.

10. Compounds as claimed in claim 1, wherein R is a triazole, imidazole, pyrazole, pyridinium, pyrimidine, pyrazine, thiazole, thiazine, thiadiazole or triazine group or a quaternary derivative thereof when the R group contains a second nitrogen atom.

11. Compounds as claimed in claim 10, wherein the quaternary derivative is a C$_{1-4}$ alkyl derivative.

12. Compounds as claimed in claim 3, wherein n is 3.

13. Compounds as claimed in claim 3, wherein n is 2.

14. A method of treatment or a human or non-human body to combat bacterial infections comprising administration of an effective amount of a compound as claimed in claim 3.

15. Compounds as claimed in claim 4, wherein n is 2 or 3.

16. Compounds as claimed in claim 4, wherein n is 2.

17. A method of treatment or a human or non-human body to combat bacterial infection comprising administration of an effective amount of a compound as claimed in claim 4.

18. A method of treatment or a human or non-human body to combat bacterial infections comprising administration of an effective amount of a compound as claimed in claim 5.

19. A method of treatment or a human or non-human body to combat bacterial infections comprising administration of an effective amount of a compound as claimed in claim 6.

20. (4S,8S,9R,10S,12R)-10-(1-hydroxyethyl)-11-oxo-4-[2-(1,2,3-triazole-1-yl)ethoxy)]1-azatricyclo[7.2.0.0$^{3,8}$]undec-2-ene-2-carboxylic acid, salts thereof, or (4S,8S,9R, 10S,12R)-4-[2-(N-pyridinium)ethoxy]10-(1-hydroxyethyl)-11-oxo-1-azatricyclo[7.2.0.0$^{3,8}$]undec-2-ene-2-carboxylate.

21. A compound as claimed in claim 14 which is a potassium or sodium salt.

* * * * *